United States Patent [19]
Wickramasinghe

[11] 4,435,985
[45] Mar. 13, 1984

[54] ACOUSTIC COUPLING DEVICE

[75] Inventor: Hemantha K. Wickramasinghe, London, England

[73] Assignee: National Research Development Corporation, London, England

[21] Appl. No.: 368,811

[22] Filed: Apr. 15, 1982

[30] Foreign Application Priority Data

Apr. 16, 1981 [GB] United Kingdom ............... 8112014

[51] Int. Cl.³ ............................................. G01N 29/00
[52] U.S. Cl. ........................................ 73/642; 73/606; 73/644
[58] Field of Search ....................... 73/606, 642, 644

[56] References Cited

U.S. PATENT DOCUMENTS

| | | | |
|---|---|---|---|
| 2,525,873 | 10/1950 | DeLano, Jr. ....................... | 73/606 |
| 3,663,842 | 5/1972 | Miller .................................. | 73/642 |
| 4,028,933 | 6/1977 | Lemons et al. | |
| 4,205,686 | 6/1980 | Harris et al. ........................ | 73/644 |

OTHER PUBLICATIONS

Acoustic Microscopy of Interior Planes by V. B. Jipson, Appl. Phys. Lett. 35 (5), Sep. 1, 1979, pp. 385–387.
Reflective Geometry for Microscopy and NDT, by S. Bennett et al., 1977, Ultrasonics Symposium Proceedings, 4 pages.
Acoustic Microscopy: Imaging Microelectronic Circuits with Liquid Metals, J. Attal, pp. 99–118.

*Primary Examiner*—Howard A. Birmiel
*Attorney, Agent, or Firm*—Cushman, Darby & Cushman

[57] ABSTRACT

An acoustic coupling device for use in a scanning acoustic microscope consists of an acoustic lens which has a concave focusing surface, and an acoustic coupler having a convex surface on which a convergent beam of acoustic radiation is normally incident. The coupler has a coupling surface which conforms to the shape of a test object; the coupler may be disposable. The spacing between the concave and convex surfaces may be varied to give a variable-focus device.

9 Claims, 4 Drawing Figures

ACOUSTIC COUPLING DEVICE

In scanning acoustic microscopy, when a beam of acoustic radiation passes from a solid into a coupling liquid, often water, the large difference in the velocities of sound in the solid and in water is utilised to assist infocusing the beam. But when a convergent beam passes from the coupling liquid into a solid, the velocity difference causes considerable spherical aberration, resulting in a focal spot of a diameter which is several times the diffraction limited value.

In Applied Physics Letters 35 (5) 1 September 1979 pp 385 to 387, Jipson discloses the use of gallium as a coupling liquid. The longitudinal acoustic velocity in gallium is then a better match to the shear velocity in the solid than with water-coupling so that spherical aberration is considerably reduced, but the match is rarely perfect and is better for some materials under investigation than for others. In a different approach, in 1977 Ultrasonics Symposium Proceedings IEEE cat. 77CH 1264-ISU, Bennett, Payne and Ash disclose an aspheric lens using reflective geometry.

In both of the prior art arrangements, the focal length of the device is fixed. It is an object of the present invention to provide an improved coupling device of negligible spherical aberration which, in some embodiments, has a variable focal length.

According to the invention, an acoustic coupling device comprises an acoustic lens arranged to provide a convergent beam of acoustic radiation; and an acoustic coupler having, adjacent and spaced from the acoustic lens, a convex surface over which the convergent beam of acoustic radiation is incident in an approximately normal direction, the coupler having opposite its convex surface a coupling surface which conforms to the surface of an object to be investigated.

Preferably the acoustic coupler is made of a material in which the velocity of sound is approximately equal to the velocity of sound in the object. Usually the acoustic lens will have a concave focusing surface.

In use there will be a first coupling liquid between the acoustic lens and the acoustic coupler, the liquid being such that the ratio of velocities of sound in the acoustic lens and in the liquid is high, e.g. greater than 3 and there will also be a very thin layer of a second, low loss, coupling liquid between the acoustic coupler and the object; this second layer is preferably of a thickness which is less than the wavelength of the acoustic radiation.

The main application of an acoustic coupling device will be in scanning acoustic microscopes. In a reflection mode microscope, one device will be required, while in a transmission mode microscope two such devices may be used. In a microscope there will further be provided scanning means for causing relative movement between a specimen and the convergent beam of acoustic radiation in a plane transverse to the axis of the beam, and conversion means for converting acoustic radiation received from the sample to an electrical signal which is then stored or displayed.

So far apparatus having a fixed focal length has been described. To provide a variable focus acoustic coupling device, a coupling device according to the invention further comprises means for varying the spacing between the acoustic lens and the acoustic coupler. The spacing may be varied repetitively, whereby the focus of the coupling device is scanned along the axis of the device.

The invention will now be described by way of example only with reference to the accompanying drawings in which.

Figure 1:
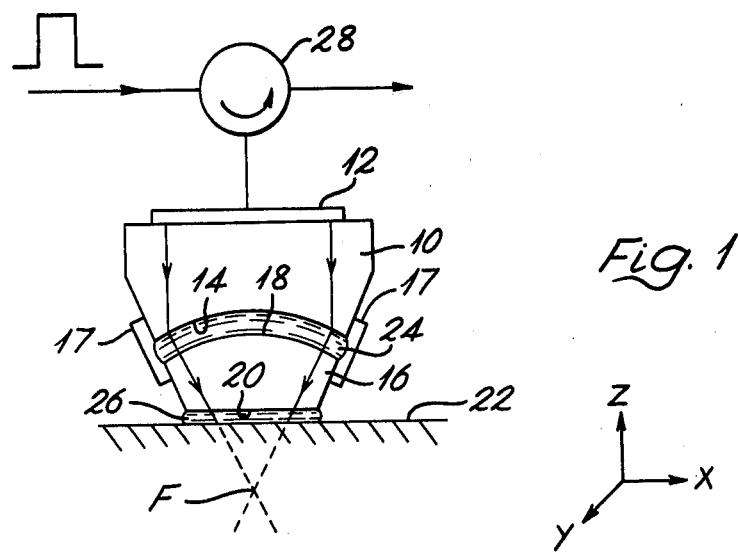
FIG. 1 is a schematic sectional diagram of an acoustic coupling device according to the invention.

In FIG. 1, an acoustic coupling device comprises a fused quartz acoustic lens 10 having on one flat surface a piezoelectric transducer 12, the opposite surface 14 having spherically concave. Spaced from the concave surface is an aluminium acoustic coupler 16, its surface 18 adjacent the lens 10 being spherically convex, and the opposite, coupling, surface 20 conforming to the surface of an aluminium object 22. In the Figure the object surface and therefore the coupling surface 20 are both plane. The coupler 16 is attached to the lens 10 by mechanical supports 17, shown schematically. The supports allow easy removal and replacement of the coupler 16.

Between the concave and convex surfaces 14, 18 is a layer 24 of a first coupling liquid, and between the coupling surface 20 and the object 22 is a second, low loss, coupling liquid layer 26. Water may be used in both cases. The second layer 26 is of a thickness which is less than the wavelength of sound in water.

The transducer 12 is connected to a pulsed high frequency source and to a signal storage or display device (not shown) through a gating system 28.

In operation the source supplies the transducer 12 with an electrical signal, typically at 0.1 gigahertz, and the transducer 12 generates acoustic radiation having plane wavefronts in the quartz lens 10. At the concave surface 14 the radiation passes into the water 24 and, since the ratio of acoustic velocities in quartz and water is high, the radiation is focused at a position F spaced a short distance from the lens 10. The convergent beam in the water 24 is incident on the convex surface 18 in a normal direction over the whole of the surface so that as the radiation enters the aluminium coupler no spherical aberration is introduced into the convergent beam. The convergent beam passes from the aluminium coupler 16 through the thin layer of water 26 into the aluminium object 22. Since the velocity of sound is identical in the coupler 16 and in the object 22, and since the water layer 26 is so thin, minimal spherical aberration is introduced. The dimensions are such that the focus F is within the object 22 at a known distance below the surface.

If relative motion between the focus F and the object 22 is generated in the X-Y plane (indicated in the Figure), and if acoustic radiation received from the focal point F is converted to an electrical signal, an aberration-free image of the object at a constant depth below its surface can be generated by the signal storage and display device.

In the coupling device illustrated in FIG. 1, the entire focusing effect occurs at the concave quartz/water interface 14. Acoustic radiation passes from that interface of the focus F without further deviation, because the acoustic velocities in the coupler 16 and the sample 22 are identical. Since, as will be shown later, the arrangement allows considerable tolerance, this velocity match need not be precise; the coupler need not be of the same material as the object, provided a reasonable velocity match is provided. It is a further requirement that the coupling surface 22 of the coupler 20 must match the surface of the object, and can be either concave or convex or plane. It is therefore a feature of the invention that, while the lens 10, transducer 12 etc., will be of a permanent nature, an acoustic coupler 15 may be disposable, that is, constructed of a suitable material having the correct acoustic velocity to match approximately any particular sample, and being of a material which is cheap and easy to machine to follow any sample surface curvature. The surface match must give contours differing by less than the wavelength of the acoustic radiation.

It will also be clear that, from the known property of the concave solid/liquid focusing interface, while the surfaces 14 and 18 are both spherical, they are not arranged to be concentric; the relative position is determined by the requirement of normal incidence on the convex surface 18.

Figure 2:
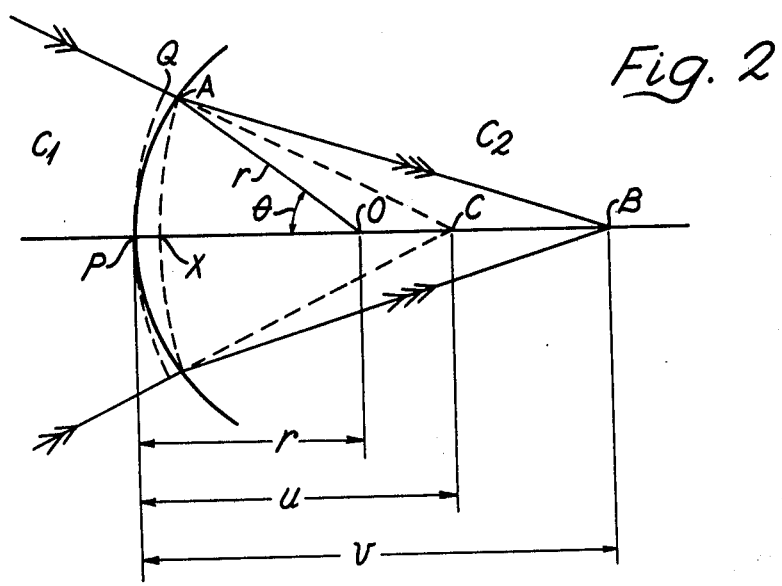
FIG. 2 is a ray diagram indicating the variable focus of the acoustic coupling device.

Referring now also to FIG. 2, let the solid curve PA represent the convex surface 18 of the coupler 16 having its centre of curvature at O, where the radius AO is of length r and makes an angle $\theta$ with the axis. Broken curve PQ represents the wavefront of a spherical wave in the first coupling liquid 24 with centre of curvature at C, and the incoming radiation is represented by the double-arrowed lines. Within the coupler, broken curve AX represents the reference wavefront which comes to a perfect focus at B; the radiation path is indicated by the triple-arrowed lines. The distances of axial points O, C and B from the point P are respectively r, u and v.

The spherical aberration $W(\theta)$ is obtained from Fermat's principle:

$$W(\theta) = PX - QA/\mu \qquad (1)$$

where $\mu = C_1/C_2$ is the ratio of the longitudinal velocity of sound in the water 24 to the longitudinal, (or shear), velocity in the solid 16.

Now $AB = [2r^2(1-\cos\theta) - 2vr(1-\cos\theta) + v^2]^{\frac{1}{2}}$ (2)

and $AC = [2r^2(1-\cos\theta) - 2ur(1-\cos\theta) + u^2]^{\frac{1}{2}}$ (3)

Also, v can be obtained using the paraxial lens formula for a single surface:

$$v = \frac{\mu u r}{r + (\mu - 1)u} \qquad (4)$$

When the incident wavefront PQ matches the spherical surface on element (2), (i.e. $u=r$ and the spherical aberration is zero), equation (4) yields:

$$v = u = r \qquad (5)$$

Consider the situation where u is perturbed about its ideal value $u=r$. Let us take $u = r(1+\Delta)$. The equation (4) gives:

$$v = \frac{\mu(1+\Delta)r}{\mu + \Delta(\mu - 1)} \qquad (6)$$

The corresponding perturbation v is given by:

$$\delta v = \frac{\Delta r}{\mu + \Delta(\mu - 1)} \qquad (7)$$

Inserting equations (2), (3) and (6) into equation (1) yields an expression for the spherical aberration $W(\theta)$:

$$\frac{W(\theta)}{r} = (\Delta + 1)\left[\frac{\mu}{\mu + (\mu - 1)\Delta} - \frac{1}{\mu}\right] - \qquad (8)$$

$$\left[\frac{(\Delta + 1)^2 \mu^2}{[\mu + (\mu - 1)\Delta]^2} - \frac{4\Delta\sin^2(\theta/2)}{\mu + (\mu - 1)\Delta}\right]^{\frac{1}{2}} +$$

$$\frac{1}{\mu}[(\Delta + 1)^2 - 4\Delta\sin^2(\theta/2)]^{\frac{1}{2}}$$

As expected, equation (8) predicts that $W(\theta) \to 0$ both as $\theta \to 0$ and as $\Delta \to 0$.

Consider now a typical case. For a water/aluminium interface, $\mu = 0.25$ and the numerical aperture of the lens 10 may be 0.25 or 0.5 within the object. In Table 1, $W(\theta max/r)$ is calculated for several values of $\Delta$. In Table 2, similar calculations are made for a galluim/aluminium interface when $\mu = 0.5$.

TABLE 1

NORMALISED SPHERICAL ABERRATION AS A FUNCTION OF $\Delta$ FOR A WATER ALUMINIUM INTERFACE ($\mu = 0.25$)

| $\Delta$ | $W(\theta_{max})/r$ (NA = 0.25) | $W(\theta_{max})/r$ (NA = 0.5) |
|---|---|---|
| 1/50 | $2.1 \times 10^{-6}$ | $37.8 \times 10^{-6}$ |
| 1/40 | $3.2 \times 10^{-6}$ | $57.1 \times 10^{-6}$ |
| 1/30 | $5.3 \times 10^{-6}$ | $95.8 \times 10^{-6}$ |
| 1/20 | $10.5 \times 10^{-6}$ | $191.1 \times 10^{-6}$ |
| 1/10 | $27.5 \times 10^{-6}$ | $506.8 \times 10^{-6}$ |

TABLE 2

NORMALISED SPHERICAL ABERRATION AS A FUNCTION OF $\Delta$ FOR A GALLIUM/ALUMINIUM INTERFACE ($\mu = 0.5$)

| $\Delta$ | $W(\theta_{max})/r$ (NA = 0.25) | $W(\theta_{max})/r$ (NA = 0.5) |
|---|---|---|
| 1/50 | $4 \times 10^{-7}$ | $6.5 \times 10^{-6}$ |
| 1/40 | $6 \times 10^{-7}$ | $10 \times 10^{-6}$ |
| 1/30 | $1 \times 10^{-6}$ | $17.1 \times 10^{-6}$ |
| 1/20 | $2 \times 10^{-6}$ | $35.5 \times 10^{-6}$ |
| 1/10 | $6.1 \times 10^{-6}$ | $111.3 \times 10^{-6}$ |

From Tables 1 and 2 it is clear that for all cases considered, the spherical aberration is negligible; in the worst case, $W(\theta_{max})/r$ is about $0.5 \times 10^{-3}$ for $\Delta = 0.1$.

This discovery leads to an important modification. If the lens 10 is axially scanned (i.e. in the Z direction) so that the focal point F is also axially scanned, an image having negligible spherical aberration is still obtainable. This allows the depth of focus under the surface of the object to be selected and varied over a considerable range for a single acoustic coupling device. Such an arrangement is completely new in scanning acoustic microscopes and is illustrated schematically in FIG. 3.

Figure 3:
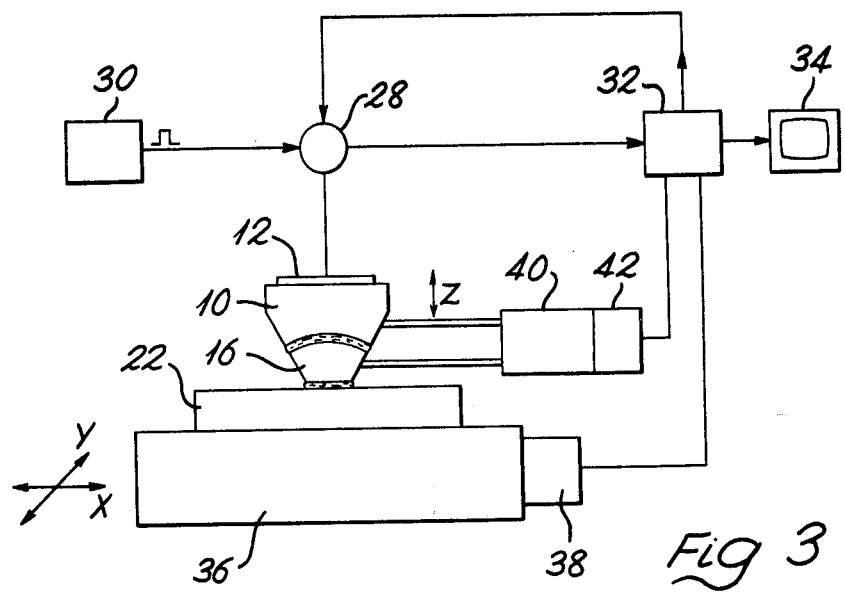
FIG. 3 is a schematic diagram of a scanning acoustic microscope using a coupling device according to the invention.

In FIG. 3, the acoustic lens 10 and transducer 12, the acoustic coupler 16, and the specimen 22 are illustrated as before. The transducer 12 is connected through the gating device 28 to a pulsed high frequency source 30. The gating device 28 is controlled by a control and storage circuit 32 which also receives signals from the transducer 12 and supplies modified signals to a display unit 34.

The specimen 22 is supported by a mechanical support 36 which can be scanned in one or both directions in the X-Y plane, typically at 1 Hz, by electrical X-Y scan circuit 38 which is instructed by the control circuit 32. The lens 10 and coupler 16 are each mechanically connected to a support 40 which allows scanning movement in the Z direction of the lens 10. The Z scanning movement, typically 100 Hz, is controlled by an electrical Z-scan circuit 42 which is instructed by the control circuit 32.

In operation, signals received from the transducer 12 and which contain information about the specimen 22 in the region of the focus are supplied in suitable form to the display unit 34. The control circuit 32 correlates the display position with the X-Y scan. Either images of different X-Y scans at various depths within the sample 22 can be provided, or the specimen can be scanned in the X and Z directions at a fixed Y position to give an image of an X-Z section of the specimen.

In a typical situation, for a working frequency of 100 MHz, when the wavelength in aluminium is $\lambda=60$ micrometers, Tables 1 and 2 indicate that the radius of curvature of convex surface 18 (FIG. 1) can be as large as 10 millimeters and still have negligible spherical aberration, that is, $W(\theta_{max})=5$ micrometers, less than a tenth of a wavelength. With such a device, the focus can be scanned between $\Delta=+0.1$ and $\Delta=-0.1$ which is equivalent to a distance of 8.7 millimeters, and diffraction limited resolution is still attained, even though there is a departure from the generalised requirement of normal incidence on the convex surface 18.

The device according to the invention is not limited to the materials specified. The use of gallium as a coupling liquid has already been mentioned and is advantageous in this arrangement because, with the smaller difference in velocity of sound in the solid and the liquid a greater difference from normal incidence is tolerable; glycerine and mercury are other possibilities. The acoustic lens 10 may be made of, for example, aluminium or sapphire, depending on the coupling liquid used and the depth of focus required.

Figure 4:
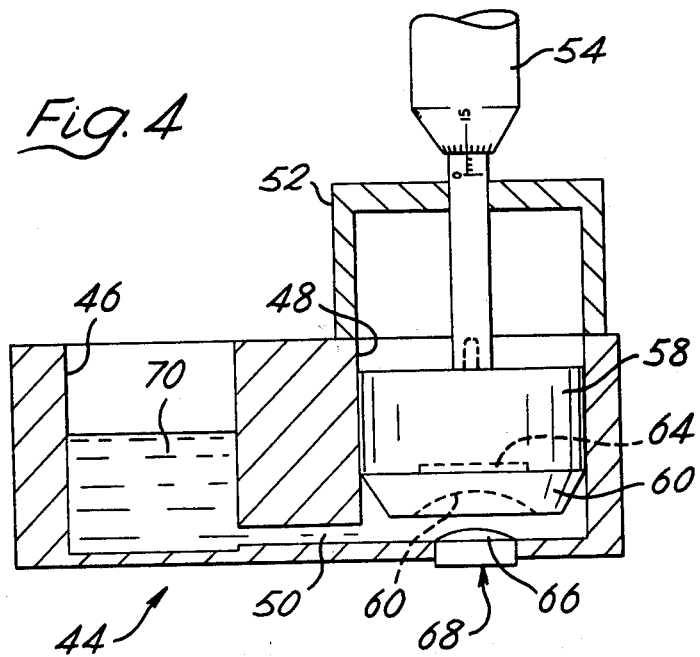
FIG. 4 is a schematic sectional diagram of an alternative acoustic coupling device according to the invention.

An embodiment using a mercury coupling liquid is illustrated in FIG. 4. An aluminium alloy block 44 has two bores 46, 48 connected by a passage 50 near the base of the block. Above the bore 48 is a bridge 52 supporting a micrometer gauge 54 the spindle 56 of which carries a support block 58 to which is attached an aluminium acoustic lens 60. The lens has a concave lower surface 62 and a plane piezoelectric transducer 64 spaced from the focusing surface 62.

Below the focusing surface 62 is an aluminium coupler 66 fixed to the aluminium block 44 and having a coupling surface 68 which protrudes below the block 44.

The bore 46 acts as a reservoir and contains mercury 70. The passage 50 and the space in the bore 48 between the lens 60 and the coupler 66 are filled with mercury which constitutes the first coupling liquid.

In use the micrometer gauge 54 is operated to adjust and measure the spacing between the lens 60 and the coupler 66. As the lens is moved up and down, mercury moves out of and into the reservoir bore 46 through the passage 50.

If necessary, the curved surfaces of the lens and the coupler in either embodiment of the invention may be provided with quarter wave antireflection coatings.

While the invention has been described with reference to an improved acoustic coupling system used in a scanning acoustic microscope operating in the reflection mode, two such systems could be used to provide a transmission scanning acoustic microscope.

I claim:

1. An acoustic coupling device comprising:
    an acoustic lens arranged to provide a convergent beam of acoustic radiation; and
    an acoustic coupler having adjacent and spaced from the acoustic lens a convex surface over which the convergent beam of radiation is incident in an approximately normal direction,
    the coupler having opposite the convex surface a coupling surface which conforms to the surface of an object to be investigated and the beam converging beyond said coupling surface;
    there being between the acoustic lens and the acoustic coupler a first coupling liquid such that the ratio of the velocity of sound in the acoustic lens and the velocity of sound in the liquid is greater than 3,
    the device also having between the acoustic coupler and the object a layer of a second, low acoustic loss, coupling liquid.

2. A coupling device according to claim 1 in which the acoustic coupler is made of a material in which the velocity of sound is approximately equal to the velocity of sound in the object to be investigated.

3. A coupling device according to claim 1 which the acoustic lens has a concave focusing surface.

4. A coupling device according to claim 1 in which the first coupling liquid is water or gallium or glycerine or mercury.

5. A coupling device according to claim 1 in which the layer of the second coupling liquid is of a thickness which is less than the wavelength of the acoustic radiation.

6. A coupling device according to claim 5 in which the second coupling liquid is water or gallium or glycerine or mercury.

7. A variable focus acoustic coupling device comprises an acoustic coupling device according to claim 1 further comprising variable support means for supporting the acoustic coupler adjacent to and at a variable distance from the acoustic lens.

8. A variable focus acoustic coupling device according to claim 7 in which the variable support is a scanning device which can repeatedly vary the distance of the acoustic coupler from the acoustic lens.

9. A scanning acoustic microscope comprising at least one acoustic coupling device which comprises,
    an acoustic lens arranged to provide a convergent beam of acoustic radiation; and an acoustic coupler having adjacent and spaced from the acoustic lens a convex surface over which the convergent beam of radiation is incident in an approximately normal direction, the coupler having opposite the convex surface a coupling surface which conforms to the surface of an object to be investigated, and the beam converging beyond said coupling surface;
    scaning means for causing relative movement between the object and the convergent beam in a plane transverse to the axis of the beam; and
    conversion means for converting acoustic radiation received from the sample to an electrical signal which is then stored or displaced.

* * * * *